(12) United States Patent
Ohmori et al.

(10) Patent No.: US 8,399,663 B2
(45) Date of Patent: Mar. 19, 2013

(54) SALT OF 1,3,5-TRIAZINE-2,4,6-TRIAMINE DERIVATIVE

(75) Inventors: Junya Ohmori, Tokyo (JP); Makoto Kasai, Tokyo (JP); Takenori Kimura, Tokyo (JP); Noritaka Hamada, Tokyo (JP); Ryo Mizoguchi, Tokyo (JP); Satoshi Miyamoto, Tokyo (JP); Noriyuki Kawano, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 75 days.

(21) Appl. No.: 12/753,415

(22) Filed: Apr. 2, 2010

(65) Prior Publication Data
US 2010/0256151 A1    Oct. 7, 2010

Related U.S. Application Data

(60) Provisional application No. 61/275,696, filed on Apr. 3, 2009.

(51) Int. Cl.
C07D 403/12    (2006.01)
A61K 31/53    (2006.01)
A61P 25/28    (2006.01)

(52) U.S. Cl. .......................... 544/198; 544/197; 514/245
(58) Field of Classification Search .................. 544/198, 544/197; 514/245
See application file for complete search history.

(56) References Cited

U.S. PATENT DOCUMENTS

| | | |
|---|---|---|
| 6,326,168 B1 | 12/2001 | Miyake et al. |
| 6,518,398 B1 | 2/2003 | Curtis |
| 7,094,948 B2 | 8/2006 | Miyake et al. |
| 7,375,222 B2 * | 5/2008 | Kubota et al. .................. 544/198 |
| 2003/0104429 A1 | 6/2003 | Curtis |
| 2007/0083334 A1 | 4/2007 | Mintz et al. |

FOREIGN PATENT DOCUMENTS

| | | |
|---|---|---|
| WO | 99-43696 A1 | 9/1999 |
| WO | 00/01819 A1 | 1/2000 |
| WO | 00/05346 A1 | 2/2000 |
| WO | 00/09534 A1 | 2/2000 |
| WO | 00/22001 A2 | 4/2000 |
| WO | 02/50066 A2 | 6/2002 |
| WO | 03-016475 A2 | 2/2003 |
| WO | 2004-071411 A2 | 8/2004 |
| WO | 2007-047796 A2 | 4/2007 |
| WO | 2007/051333 A1 | 5/2007 |
| WO | 2008-021290 A2 | 2/2008 |
| WO | 2009-133191 A1 | 11/2009 |

OTHER PUBLICATIONS

Web page published by PRA International; "Informatieblad Voor Deelname Aan Onderzoek" pp. 1-2; Apr. 8, 2008, with the letter from PRA confirming publication date of Apr. 8, 2008.
Web page by Astellas listing the past IR Information from May '05 to Feb. '09.; 4 pages.
Document explaining the situation of R&D of Astellas published on the web on May 13, 2008.
Huang et al., "In Silico Discovery of β-Secretase Inhibitors" JACS (J. Am. Chem. Soc.) Articles, Published on web Mar. 30, 2006, American Chemical Society, vol. 128, No. 16, pp. 5436-5443.
International Search Report dated Jun. 11, 2010 issued in counterpart Application No. PCT/JP2010/056143.
Written Opinion of the International Searching Authority issued in counterpart Application No. PCT/JP2010/056143.

\* cited by examiner

*Primary Examiner* — Venkataraman Balasubramanian
(74) *Attorney, Agent, or Firm* — Sughrue Mion, PLLC

(57) ABSTRACT

Anytime obtained is uniform crystal of N-(4-fluorophenyl)-N'-phenyl-N"-(pyrimidin-2-ylmethyl)-1,3,5-triazine-2,4,6-triamine (compound A) and/or N,N'-bis (4-fluorophenyl)-N"-(pyrimidin-2-ylmethyl)-1,3,5-triazine-2,4,6-triamine (compound B) as a medicament or a starting material for the preparation of the medicament, and provided are a fumarate of the compound A and/or the compound B having excellent stability and a novel crystal thereof. A salt of the compound A and/or the compound B with fumaric acid enables uniform crystal to be anytime obtained, and thus, it is a compound that is very useful as a medicament or a starting material for the preparation of the medicament having excellent stability.

5 Claims, 14 Drawing Sheets

SALT OF 1,3,5-TRIAZINE-2,4,6-TRIAMINE DERIVATIVE

TECHNICAL FIELD

The present invention relates to a medicine, particularly to a novel salt of N-(4-fluorophenyl)-N'-phenyl-N"-(pyrimidin-2-ylmethyl)-1,3,5-triazine-2,4,6-triamine (hereinafter referred to as a compound A) and/or N,N'-bis(4-fluorophenyl)-N"-(pyrimidin-2-ylmethyl)-1,3,5-triazine-2,4,6-triamine (hereinafter referred to as a compound B) that is useful as a specific potassium channel inhibitor.

BACKGROUND ART

It is known that the compound A and/or the compound B has/have the following chemical structure, has/have an action of inhibiting a specific potassium channel (BEC1 potassium channel) and an anti-depression action, and is/are useful for treatment of dementia (U.S. Pat. No. 7,375,222, herein incorporated by reference).

[Chemical Formula 1]

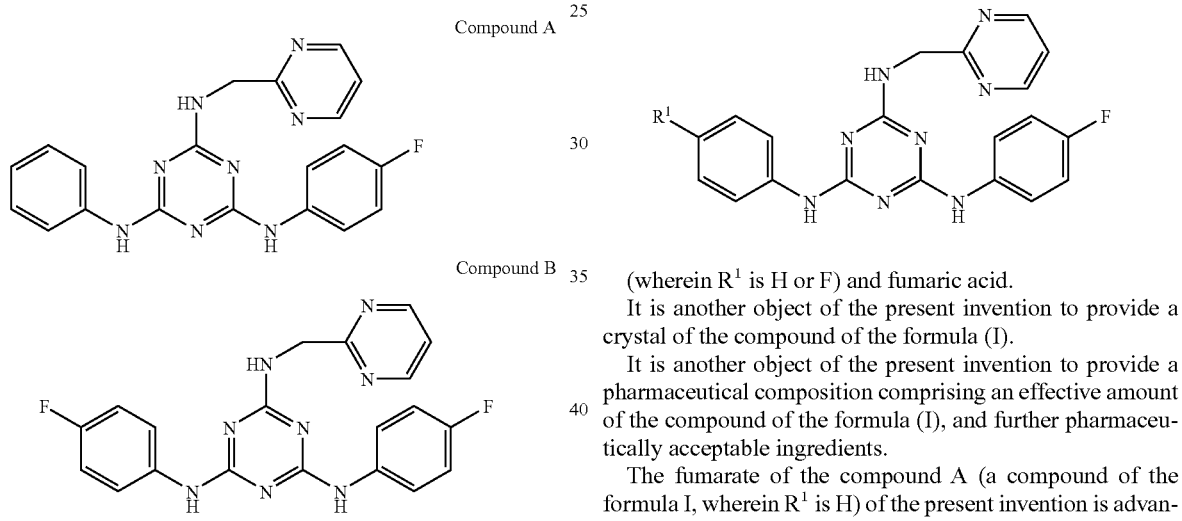

Specifically, the compound A is isolated in the composition of compound A.2 HCl.0.3H$_2$O.0.1 ethyl acetate (U.S. Pat. No. 7,375,222, herein incorporated by reference), but there is no specific report on other pharmaceutically acceptable acid addition salts. Further, the compound B is described only as paper Examples (U.S. Pat. No. 7,375,222, herein incorporated by reference).

SUMMARY OF THE INVENTION

The compound A has a pKa value of 3.9, and its basicity is weak, and in this regard, generally, it preferably forms salts with strong acids. A dihydrochloride salt of the compound A that is a known compound having a hydrogen chloride, which is one of the typical strong acids, as a counter-ion is obtained as a crystal of anhydrous, free from an residual solvent, but since a plurality of endothermic peaks can be observed in DSC analysis, there was a possibility of co-existence of some crystal forms. It is a well-known fact that even though they are compounds having the same structural formula, the solubility or stability of the compounds is different when they have different crystal forms. In order to ensure the identity of the quality or the stability of a medicament, it is preferable to select a compound and a method for the preparation thereof that enable the same crystal form to be anytime obtained.

For the compound B, the specific compound has not been available. However, the facts that in order to ensure the identity of the quality or the stability of a medicament, it is preferable to select a compound (a free base or specific acid addition salt) and a method for the preparation thereof that enables the same crystal form to be anytime obtained, and that in a case where a solvate can be obtained, it is preferably a pharmaceutically available solvate, which also applies to the compound A.

The present inventors have extensively studied on the compound A and B, or a free base or acid addition salts thereof, and as a result, they have found that a specific non-volatile acid addition salt of the compound A and/or B can be anytime obtained as uniform crystal, and that the crystal has excellent stability, thus completing the present invention.

That is, an object of the present invention is to provide a salt comprising a compound of the formula (I):

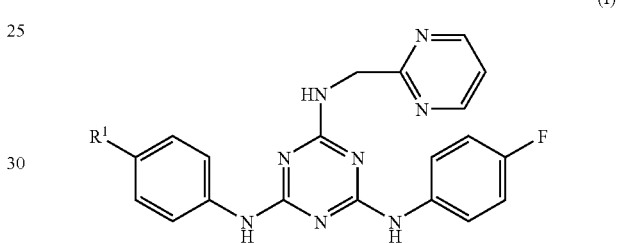

(I)

(wherein R$^1$ is H or F) and fumaric acid.

It is another object of the present invention to provide a crystal of the compound of the formula (I).

It is another object of the present invention to provide a pharmaceutical composition comprising an effective amount of the compound of the formula (I), and further pharmaceutically acceptable ingredients.

The fumarate of the compound A (a compound of the formula I, wherein R$^1$ is H) of the present invention is advantageous in that it enables uniform crystal to be anytime obtained, as compared to the dihydrochloride salt of the compound A that is a known compound, and is an extremely useful compound as a medicament or an active pharmaceutical ingredient having excellent stability. Further, the fumarate of the compound B (a compound of the formula I, wherein R$^1$ is F) of the present invention also enables uniform crystal to be anytime obtained, and is an extremely useful compound as a medicament or an active pharmaceutical ingredient having excellent stability.

Particularly, it is disclosed that in terms of a fact that uniform crystal is anytime obtained, the dihydrochloride salt of the compound A that is a known compound does not enable uniform crystal to be obtained, and in a case of selecting a developed product, it is disadvantageous that it is inevitably required to anytime prepare a crystal having a certain range of specifications of solubility or stability. The fumarate of the compound A and/or B contributes the provision of an excellent medicament, since that it enables uniform crystal to be anytime obtained, and the crystal exhibits excellent stability.

The compound A and/or compound B inhibits methamphetamine-induced hyperlocomotion that is an animal model of Schizophrenia. That is, it was found that these two compounds have an effect of improving dementia, as well as an action of improving the symptoms of Schizophrenia.

BRIEF DESCRIPTION OF THE DRAWINGS

By way of example and to make the description more clear, reference is made to the accompanying drawing in which.

DETAILED DESCRIPTION OF THE PRESENT INVENTION

Figure 1:
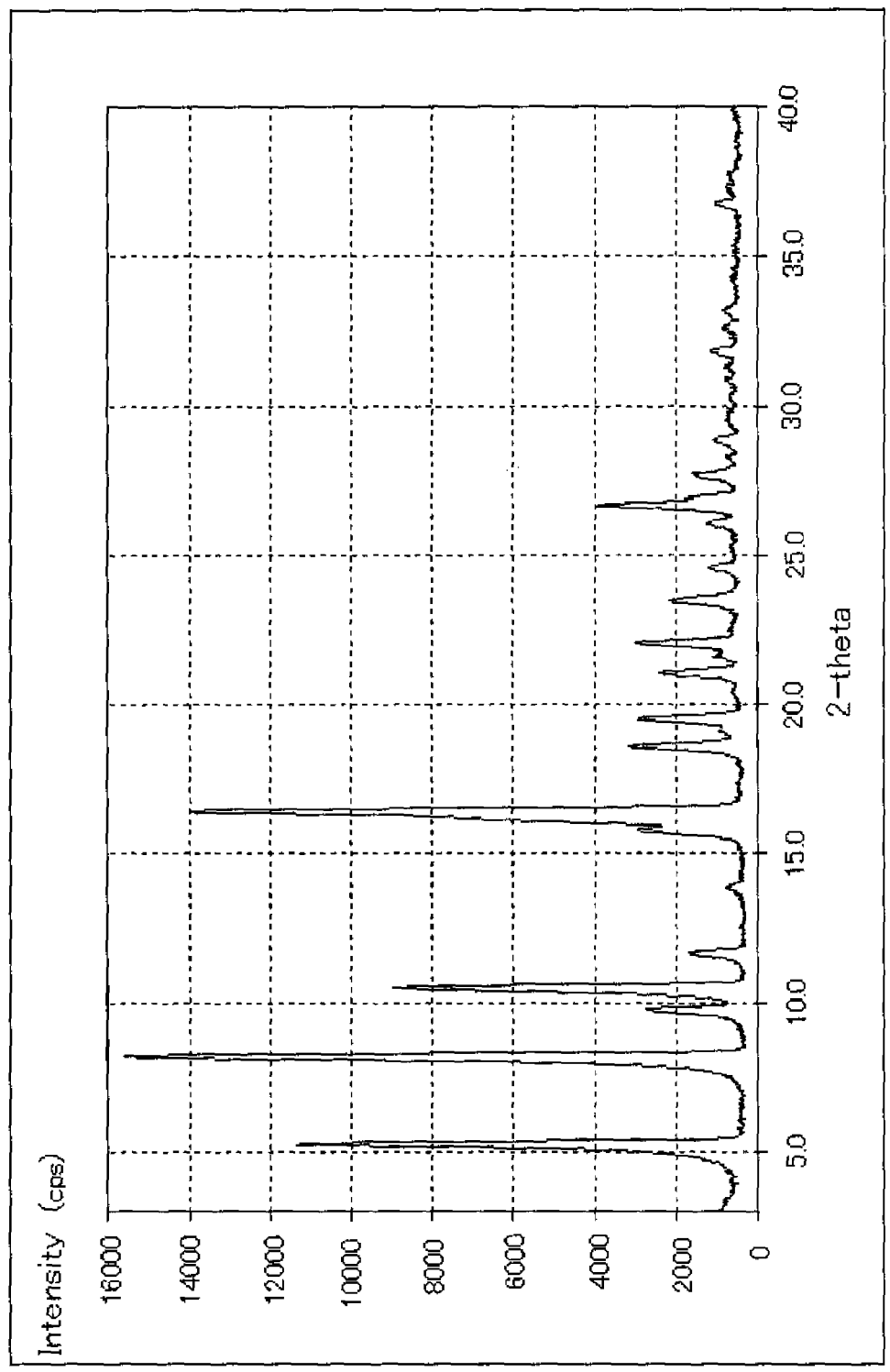
FIG. 1 is a graph showing the powder X-ray diffraction pattern of a crystal of an anhydrous salt having a ratio of the compound A to fumaric acid of 2:1 (type I crystal).

The fumarate of the compound A and/or the fumarate of the compound B of the present invention enables uniform crystal to be anytime obtained, and the crystal exhibits excellent stability. Thus, any salt or crystal thereof of the present invention is suitable for a medicament or an active pharmaceutical ingredient, and particularly preferred is a salt having a ratio of the compound A to fumaric acid of 2:1 and/or a salt having a ratio of the compound B to fumaric acid of 1:1, or a crystal thereof.

Preferred embodiments of the present invention are shown below.

(1) An anhydrous salt having a ratio of the compound A to fumaric acid of 2:1.

(2) A crystal of an anhydrous salt having a ratio of the compound A to fumaric acid of 2:1.

(3) The crystal as described in (2), wherein the endothermic onset temperature in DSC is around 190° C.

(4) The crystal as described in (2), which is characterized in that in the powder X-ray analysis using Cu as an anode, 2θ (°) shows the peaks at around 5.3, around 8.2, around 10.5 and around 16.4.

(5) The crystal as described in (2), which is characterized in that in the powder X-ray analysis using Cu as an anode, 2θ (°) shows the peaks at around 5.3, around 8.2, around 9.8, around 10.5, around 11.7, around 16.4, around 18.6 and around 26.6.

(6) The crystal as described in (2), which is characterized in that the endothermic onset temperature in DSC is from 180 to 200° C., and in the powder X-ray analysis using Cu as an anode, 2θ (°) shows the peaks at around 5.3, around 8.2, around 10.5 and around 16.4.

(7) The crystal as described in (2), which is characterized in that the endothermic onset temperature in DSC is from 180 to 200° C., and in the powder X-ray analysis using Cu as an anode, 2θ (°) shows the peaks at around 5.3, around 8.2, around 9.8, around 10.5, around 11.7, around 16.4, around 18.6 and around 26.6.

(8) The crystal as described in (2) to (7), which is a type I crystal.

(9) A pharmaceutical composition which includes a salt comprising the compound A and fumaric acid as an active ingredient, and further a pharmaceutically acceptable carrier.

(10) The pharmaceutical composition as described in (9), wherein the active ingredient is a salt having a ratio of the compound A to fumaric acid of 2:1.

(11) The pharmaceutical composition as described in (9), wherein the active ingredient is an anhydrous salt having a ratio of the compound A to fumaric acid of 2:1.

(12) A pharmaceutical composition including a crystal as described in (2) to (7) as an active ingredient, and further a pharmaceutically acceptable carrier.

(13) A salt having a ratio of the compound A to fumaric acid of 2:1, which is a hydrate having a ratio of the compound A to water of 2:1.

(14) A crystal of the compound as described in (13).

(15) The crystal as described in (14), wherein the endothermic onset temperature in DSC is around 150° C.

(16) The crystal as described in (14), which is characterized in that in the powder X-ray analysis using Cu as an anode, 2θ (°) shows the peaks at around 6.7, around 7.8, around 20.1 and around 20.5.

(17) The crystal as described in (14), which is characterized in that in the powder X-ray analysis using Cu as an anode, 2θ (°) shows the peaks at around 6.7, around 7.8, around 8.1, around 10.5, around 13.9, around 20.1, around 20.5 and around 21.6.

(18) The crystal as described in (14), which is characterized in that the endothermic onset temperature in DSC is from 140 to 160° C., and in the powder X-ray analysis using Cu as an anode, 2θ (°) shows the peaks at around 6.7, around 7.8, around 20.1 and around 20.5.

(19) The crystal as described in (14), which is characterized in that the endothermic onset temperature in DSC is from 140 to 160° C., and in the powder X-ray analysis using Cu as an anode, 2θ (°) shows the peaks at around 6.7, around 7.8, around 8.1, around 10.5, around 13.9, around 20.1, around 20.5 and around 21.6.

(20) The crystal described in (14) to (19), which is a type II crystal.

(21) A pharmaceutical composition including the salt as described in (13) as an active ingredient, and further a pharmaceutically acceptable carrier.

(22) A pharmaceutical composition including the crystal described in (14) to (20) as an active ingredient, and further a pharmaceutically acceptable carrier.

(23) A salt having a ratio of the compound A to fumaric acid of 1:1.

(24) An anhydrous salt having a ratio of the compound A to fumaric acid of 1:1.

(25) A crystal of the compound described in (23) or (24).

(26) The crystal as described in (25), wherein the endothermic onset temperature in DSC is around 160° C.

(27) The crystal as described in (25), which is characterized in that in the powder X-ray analysis using Cu as an anode, 2θ (°) shows the peaks at around 6.7, around 17.7, around 22.3 and around 26.3.

(28) The crystal as described in (25), which is characterized in that in the powder X-ray analysis using Cu as an anode, 2θ (°) shows the peaks at around 6.7, around 9.5, around 11.5, around 13.4, around 16.4, around 17.7, around 22.3 and around 26.3.

(29) The crystal as described in (25), which is characterized in that the endothermic onset temperature in DSC is from 150 to 170° C., and in the powder X-ray analysis using Cu as an anode, 2θ (°) shows the peaks at around 6.7, around 17.7, around 22.3 and around 26.3.

(30) The crystal as described in (25), which is characterized in that the endothermic onset temperature in DSC is from 150 to 170° C., and in the powder X-ray analysis using Cu as an anode, 2θ (°) shows the peaks at around 6.7, around 9.5, around 11.5, around 13.4, around 16.4, around 17.7, around 22.3 and around 26.3.

(31) The crystal described in (25) to (30), which is a type III crystal.

(32) A pharmaceutical composition including the salt described in (23) as an active ingredient, and further a pharmaceutically acceptable carrier.

(33) A pharmaceutical composition including the compound described in (24) as an active ingredient, and further a pharmaceutically acceptable carrier.

(34) A pharmaceutical composition including the crystal described in (25) to (31) as an active ingredient, and further a pharmaceutically acceptable carrier.

(35) An anhydrous salt wherein the ratio of the compound B to fumaric acid is 1:1.

(36) A crystal of the compound described in (35).

(37) The crystal as described in (36), wherein the endothermic onset temperature in DSC is around 215° C.

(38) The crystal as described in (36), which is characterized in that in the powder X-ray analysis using Cu as an anode, 2θ (°) shows the peaks at around 6.6, around 8.2, around 15.7 and around 26.5.

(39) The crystal as described in (36), which is characterized in that in the powder X-ray analysis using Cu as an anode, 2θ (°) shows the peaks at around 6.6, around 8.2, around 9.2, around 10.9, around 13.6, around 15.7, around 20.5 and around 26.5.

(40) The crystal as described in (36), which is characterized in that the endothermic onset temperature in DSC is from 200 to 220° C., and in the powder X-ray analysis using Cu as an anode, 2θ (°) shows the peaks at around 6.6, around 8.2, around 15.7 and around 26.5.

(41) The crystal as described in (36), which is characterized in that the endothermic onset temperature in DSC is from 205 to 225° C., and in the powder X-ray analysis using Cu as an anode, 2θ (°) shows the peaks at around 6.6, around 8.2, around 9.2, around 10.9, around 13.6, around 15.7, around 20.5 and around 26.5.

(42) The crystal described in (36) to (41), which is a type I crystal.

(43) A pharmaceutical composition including a salt comprising the compound B and fumaric acid as an active ingredient, and further a pharmaceutically acceptable carrier.

(44) A pharmaceutical composition including a salt having a ratio of the compound B and fumaric acid of 1:1 as an active ingredient, and further a pharmaceutically acceptable carrier.

(45) A pharmaceutical composition including the salt described in (35) as an active ingredient, and further a pharmaceutically acceptable carrier.

(46) A pharmaceutical composition including the crystal described in (36) to (42) as an active ingredient, and further a pharmaceutically acceptable carrier.

The fumarate of the compound of the formula (I) can form a solvate. Thus, in the present specification, conveniently, a salt that is not a solvate but may have residual solvents is described as an anhydrous salt.

The compound of the formula (I) and fumaric acid can form salts at various ratios, and accordingly, crystals of salts at various ratios may be obtained therefrom in some cases. In the verification of identity of the salt and the crystal, the ratio of the compound of the formula (I) and the fumaric acid should not be strictly interpreted, since it should not be determined in a comprehensive manner by the analysis results from elemental analysis, powder X-ray diffraction pattern, DSC, and so on. The same shall apply to these solvates.

Furthermore, in the powder X-ray diffraction pattern, due to the properties of the data, the diffraction angles or entire patterns are important for verification of the identity of a crystal, the relative intensity varies more or less depending on the orientation of the crystal growth, the particle size, and the measurement conditions, and accordingly it should not be strictly interpreted. Furthermore, the present invention encompasses a pure type I crystal, a pure type II crystal, and a pure type III crystal of the fumarate of the compound A, a pure crystal of a free base of the compound A, a pure type I crystal of the fumarate of the compound B, and a pure type I crystal of dihydrochloride salt of the compound B, and a mixture that is considered essentially equivalent to these pure crystals within the present invention.

The values obtained from various spectra have some errors resulted from the orientation of the crystal growth, the particle size, and the measurement conditions in some cases. Accordingly, in the present specification, the term "around" as used in the values of the diffraction angles (2θ) in the powder X-ray diffraction pattern largely means that it is almost the values, and preferably, it means that the values may be not more or less than the values by 0.2 (°). More preferably, it means that the values may be not more or less than the values by 0.1 (°).

Furthermore, the term "around" as used in the values of the endothermic onset temperature in DSC largely means the values of the temperature of the endothermic onset (extrapolation initiation) temperature, and preferably, it means that the values may be not more or less than the values by 2° C., more preferably, it means that the values may be not more or less than the values by 1° C.

The "crystal of an anhydrous salt having a ratio of the compound A to fumaric acid of 2:1" of the present invention can be obtained by a preparation method comprising 1) a step of isolating a crystal of a monofumarate of the compound A by recrystallization using fumaric acid in a 0.9 to 1.1 mol equivalent amount relative to the compound A, and 2) a step of suspending the obtained "salt having a ratio of the compound A to fumaric acid of 1:1" in a solvent under heating, while regulating the moisture content in the solvent to be not more than 0.5%.

1) Examples of the solvent for recrystallization that is used in a step for isolating the "crystal of an anhydrous salt having a ratio of the compound A to fumaric acid of 2:1" by carrying out the recrystallization using an equivalent molar amount of fumaric acid relative to the compound A preferably include a mixed solvent of ethanol-methyl ethyl ketone, methyl ethyl ketone, a mixed solvent of acetone-DMSO, and a mixed solvent of acetone-DMSO-ethanol. The amount of the solvent for recrystallization may be 21 to 30 parts by weight, relative to the compound A used, in a case of using a mixed solvent of ethanol-methyl ethyl ketone. The ratio of the amounts of ethanol to methyl ethyl ketone is preferably from 1:1.7 to 4.3. In a case of using methyl ethyl ketone alone, 16 to 35 parts by weight may be used relative to the compound A used. In a case of a mixed solvent of acetone-DMSO, about 50 parts by weight may be used relative to the compound A used. The ratio of acetone to DMSO is preferably approximately 50:1. In a case of a mixed solvent of acetone-DMSO-ethanol, 32 to 33 parts by weight may be used relative to the compound A used. For DMSO, it is preferable to use acetone in about 10-fold amount, and ethanol in about 11-fold amount. The recrystallization can be carried out by a known method.

2) As the solvent for suspension under heating that is used for a step of suspending the "salt having a ratio of the compound A to fumaric acid of 1:1" in a solvent, while regulating the moisture content to no more than 0.5%, preferred is, for example, ethanol. For the amount of the solvent for suspension under heating is, in a case of ethanol, 10 to 20 parts by weight may be used relative to the compound A used, and the heating temperature is preferably from 50° C. to 75° C.

The "crystal of an anhydrous salt having a ratio of the compound A to fumaric acid of 2:1" of the present invention can also be obtained by the preparation method in which the compound A with 0.9 to 1.1 mol equivalent amount of fumaric acid relative to the compound A is suspended in a solvent under heating, while regulating the moisture content in the solvent to no more than 0.5%. As the solvent for suspension under heating, preferred is, for example, ethanol. For the amount of the solvent, in a case of ethanol, approximately 20 parts by weight may be used relative to the compound A used, and the heating temperature is preferably from 60° C. to 70° C.

The "crystal of the salt having a ratio of the compound A to fumaric acid of 2:1, which is a hydrate having a ratio of the compound A to water of 2:1" of the present invention can be obtained by a preparation method comprising 1) a step of isolating the "crystal of the salt having a ratio of the compound A to fumaric acid of 1:1" by recrystallization using fumaric acid in a 0.9 to 1.1 mol equivalent amount relative to the compound A, and 2) a step of suspending the obtained "crystal of the salt having a ratio of the compound A to fumaric acid of 1:1" in a solvent under heating, while regulating the moisture content to be not less than 5%.

1) The conditions of the solvent, and so on that are used in a step for isolating the "crystal of the salt having a ratio of the compound A to fumaric acid of 1:1" by carrying out the recrystallization using an equivalent molar amount of fumaric acid relative to the compound A are as described above.

2) As the solvent for suspension under heating that is used in the step of suspending the "crystal of the salt having a ratio of the compound A to fumaric acid of 1:1" in a solvent, while regulating the moisture content to no less than 5%, preferred is, for example, ethanol. For the amount of the solvent for suspension under heating, in a case of ethanol, approximately 10 parts by weight may be used relative to the "crystal of the salt having a ratio of the compound A to fumaric acid of 1:1", and the heating temperature is preferably from 55° C. to 65° C.

The "crystal of the salt having a ratio of the compound A to fumaric acid of 2:1, which is a hydrate having a ratio of the compound A to water of 2:1" of the present invention can also be obtained by a step in which a crystal of the compound A with 0.5 to 0.6 mol equivalent amount of fumaric acid relative to the compound A is subjected to recrystallization, while regulating the moisture content in the solvent to no less than 1%. The recrystallization can be carried out by a known method.

Examples of the solvent for recrystallization that is used in a step for isolating the "crystal of the salt having a ratio of the compound A to fumaric acid of 2:1, which is a hydrate having a ratio of the compound A to water of 2:1" by carrying out the recrystallization using fumaric acid in a 0.5 to 0.6 mol equivalent amount relative to the compound A preferably include ethanol, a mixed solvent of DMSO-water, a mixed solvent of DMSO-acetone-water, and a mixed solvent of DMSO-acetonitrile-water. It is preferable to use the solvent for recrystallization in an amount of 55 parts by weight, relative to the compound A used, in a case of ethanol having a moisture content of 1%. The amount of the solvent for recrystallization may be, in a case of a mixed solvent of DMSO-water, approximately 8 parts by weight, relative to the compound A used. The ratio of DMSO to water is preferably approximately 3:1. In a case of a mixed solvent of DMSO-acetone-water, an amount of approximately 23 parts by weight, relative to the compound A used, may be used. The ratio of DMSO to acetone to water is preferably approximately 1:2.5:2.3. In a case of a mixed solvent of DMSO-acetonitrile-water, an amount of about 15 parts by weight, relative to the compound A used, may be used. The ratio of DMSO to acetonitrile to water is preferably about 1:2.5:0.25.

The fumarate of the compound A and/or the fumarate of compound B of the present invention are used as an active ingredient, that is, the preparation including the fumarate of the compound A or the fumarate of compound B of the present invention can be used to prepare a medicament in combination with a pharmaceutically acceptable carrier, an excipient, and so on. The preparation of the medicament can be carried out in accordance with a method that is usually used in the art.

The medicament including the fumarate of the compound A or the fumarate of compound B of the present invention may be in any form of the preparations for oral administration via tablets, pills, capsules, granules, powders, solutions or so on, and of the preparations for parenteral administration via injections such as intraarticular, intravenous, or intramuscular injections, suppositories, percutaneous preparations, ointments, transdermal patches, transmucosal liquid preparations, transmucosal patches, inhalations, and so on. Particularly, the preparations for oral administration via tablets, pills, capsules, granules, and powders having a crystal of an acid addition salt of the compound A as a starting material for the preparation are advantageous as stable solid preparations.

Regarding the solid composition of the present invention for oral administration, one or more kinds of active ingredients are mixed with at least one inactive diluent such as lactose, mannitol, glucose, hydroxypropylcellulose, microcrystalline cellulose, starch, polyvinyl pyrrolidone, and/or magnesium aluminometasilicate. In a conventional method, the composition may contain inactive additives like a lubricant such as magnesium stearate, a disintegrator such as calcium cellulose glycolate, a stabilizing agent, and a dissolution auxiliary, in addition to the diluent. As occasion demands, tablets or pills may be coated with a film of a sugar coating, or a gastric or enteric coating agent, such as of sucrose, gelatin, hydroxypropylcellulose, hydroxypropylmethylcellulose phthalate, and so on.

The liquid compositions for oral administration include pharmaceutically acceptable emulsions, solutions, suspensions, syrups, elixirs, or so on, and contain a generally used inert diluent, such as purified water and ethanol. In addition to the inert diluent, this composition may contain an auxiliary agent such as a moistening agent, and a suspending agent, a sweetener, a flavoring agent, an aromatic agent, and an antiseptic.

Injections for parenteral administration include sterile aqueous or non-aqueous liquid preparations, suspensions and emulsions. As the aqueous solvent and suspension, for example, distilled water for injection and physiological saline are included. Examples of the non-aqueous solvent and suspension include propylene glycol, polyethylene glycol, plant oils such as olive oil, alcohols such as ethanol, and Polysorbate 80 (Pharmacopeia). This composition may further contain an auxiliary agent such as an antiseptic, a moistening agent, an emulsifying agent, a dispersing agent, a stabilizing agent, a dissolution auxiliary, and so on. These are sterilized, for example, by filtration through a bacteria retaining filter, blending of a bactericide, or irradiation. In addition, these can also be used by producing a sterile solid composition, and dissolving it in sterile water or a sterile solvent for injection prior to its use.

Since the pharmaceutical composition of the present invention contains the fumarate of the compound A and/or the fumarate of the compound B that is a BEC1 potassium channel inhibitor, as its active ingredient, it can be provided for treatment or prevention of various diseases involving the use of a BEC1 potassium channel inhibitor. That is, the pharmaceutical composition of the present invention is specifically useful as an agent for treating or preventing, for example, dementia.

The pharmaceutical agent used in the present invention is administered to a patient with dementia, and in oral administration, the daily dose is suitably from about 0.001 to 100 mg/kg per body weight, and this is administered in one portion or dividing it into 2 to 4 portions. In the case of intravenous administration, the daily dose is suitably from about 0.0001 to 10 mg/kg per body weight, and this is administered once a day or two or more times a day. In addition, a transmucosal agent is administered at a dose from about 0.001 to 100 mg/kg per body weight, and this is administered once a day or two or more times a day. The dose is appropriately decided in response to an individual case by taking the symptoms, the age, and the gender of the subject, and so on into consideration.

EXAMPLES

Hereinbelow, the present invention is described in detail with reference to Examples, but the present invention is not intended to be limited by Examples, and the scope of the present invention is not limited thereto.

Furthermore, the thermal analysis and the powder X-ray diffraction were carried out in the following methods.
(1) Thermal Analysis
(DSC)

Approximately 3 mg of a sample was settled in an exclusively-used aluminum-made sample pan, and the change in calories generated between the sample and a reference (an empty aluminum-made sample pan), with a measurement range from room temperature to 300° C. under a nitrogen atmosphere (50 mL/min) and a temperature elevating rate of 10° C./min were continuously measured and recorded. Furthermore, the handling of the devices including data processing was conducted in accordance to the methods and procedures as indicated in each device. (Device: Hi-Res DSC 2910, DSC Q20, manufactured by TA Instrument)
(TG)

Approximately 5 mg of a sample was settled in an exclusively-used platinum-made sample pan, and the change in the weights of the sample, with a measurement range from room temperature to 300° C. under a nitrogen atmosphere (50 mL/min) and a temperature elevating rate of 10° C./min were measured and recorded in the following conditions. Furthermore, the handling of the devices including data processing was conducted in accordance to the methods and procedures as indicated in each device. (Device: Hi-Res TGA 2950, TGA Q50, manufactured by TA Instrument)
(2) Powder X-Ray Diffraction Approximately 10 mg of a sample was settled in an exclusively-used sample holder (width 5 mm, length 18 mm, and depth 0.2 mm), and the powder X-ray diffraction pattern of the sample was continuously measured and recorded under following conditions. Furthermore, the handling of the devices including data processing was conducted in accordance to the methods and procedures as indicated in each device. (Device: MXP18TAHF22 manufactured by MAC Science (presently name: Bruker))
(Conditions)

Figure 3:
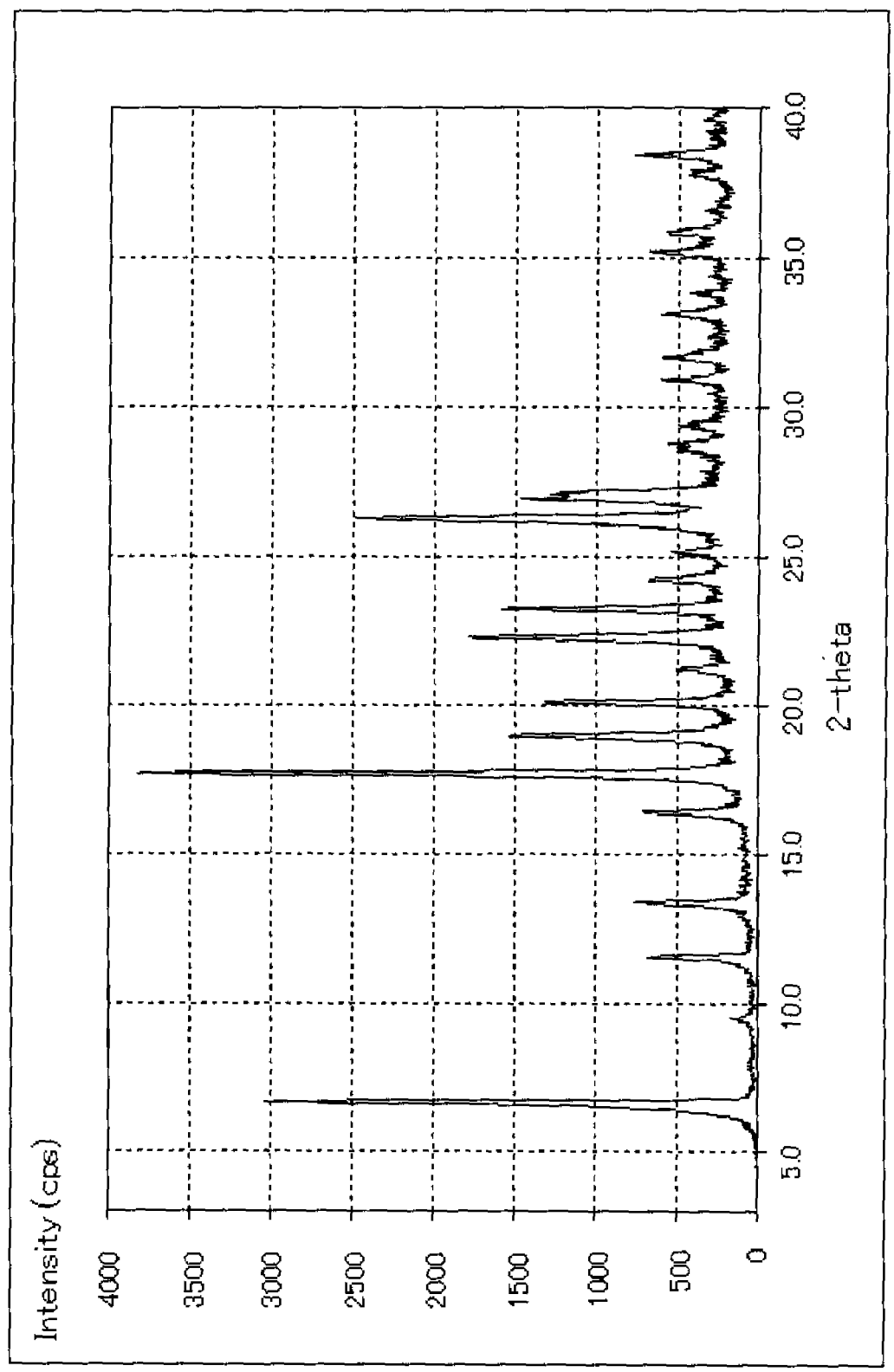
FIG. 3 is a graph showing the powder X-ray diffraction pattern of a crystal of a salt having a ratio of the compound A to fumaric acid of 1:1 (the ratio of the compound A to methyl ethyl ketone to EtOH to water that are residual solvents=1: 0.1:0.007:0.3) (type III crystal).
Figure 4:
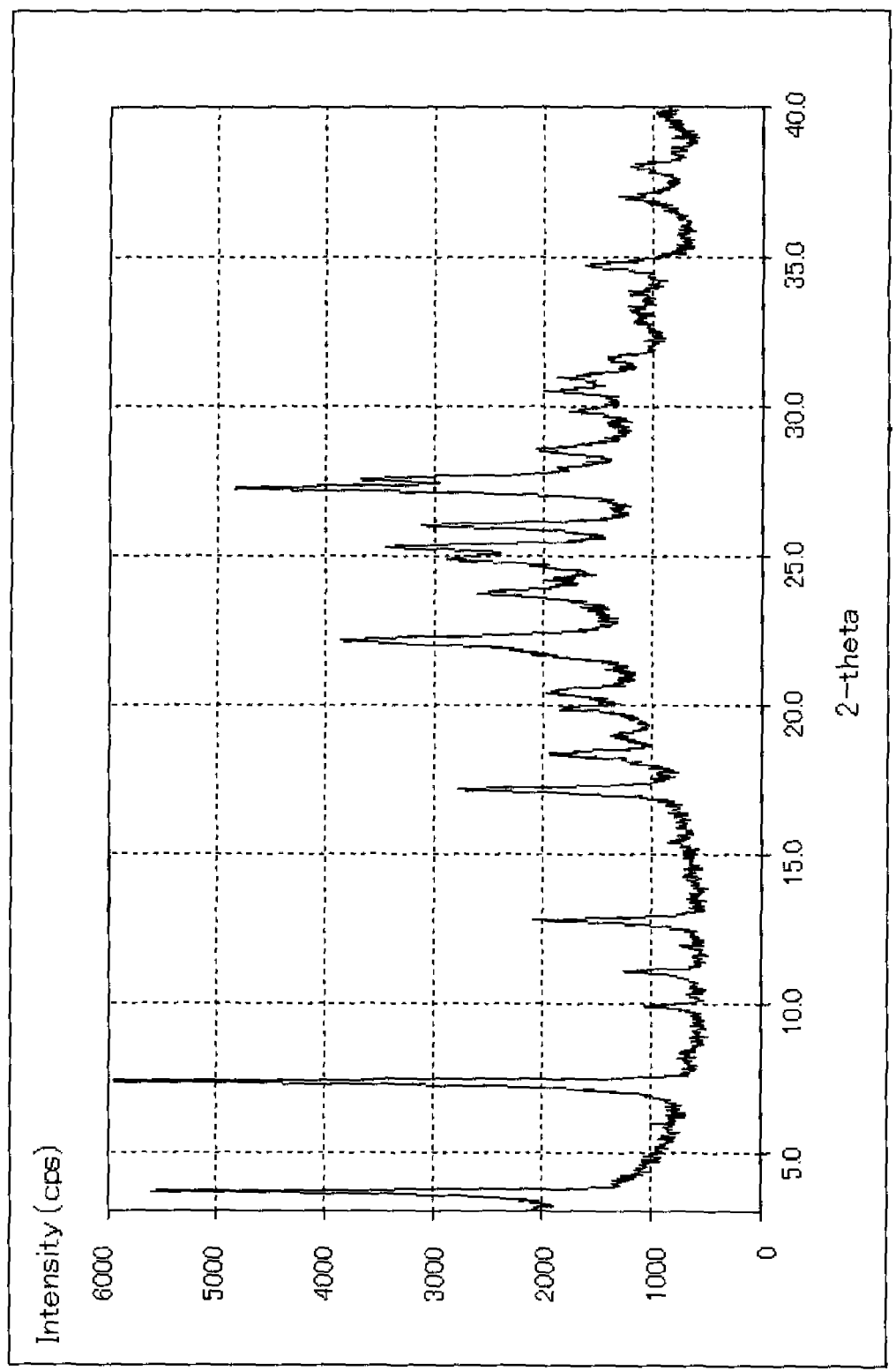
FIG. 4 is a graph showing the powder X-ray diffraction pattern of a crystal of an anhydrous salt having a ratio of the compound A to hydrogen chloride of 1:2.
Figure 13:
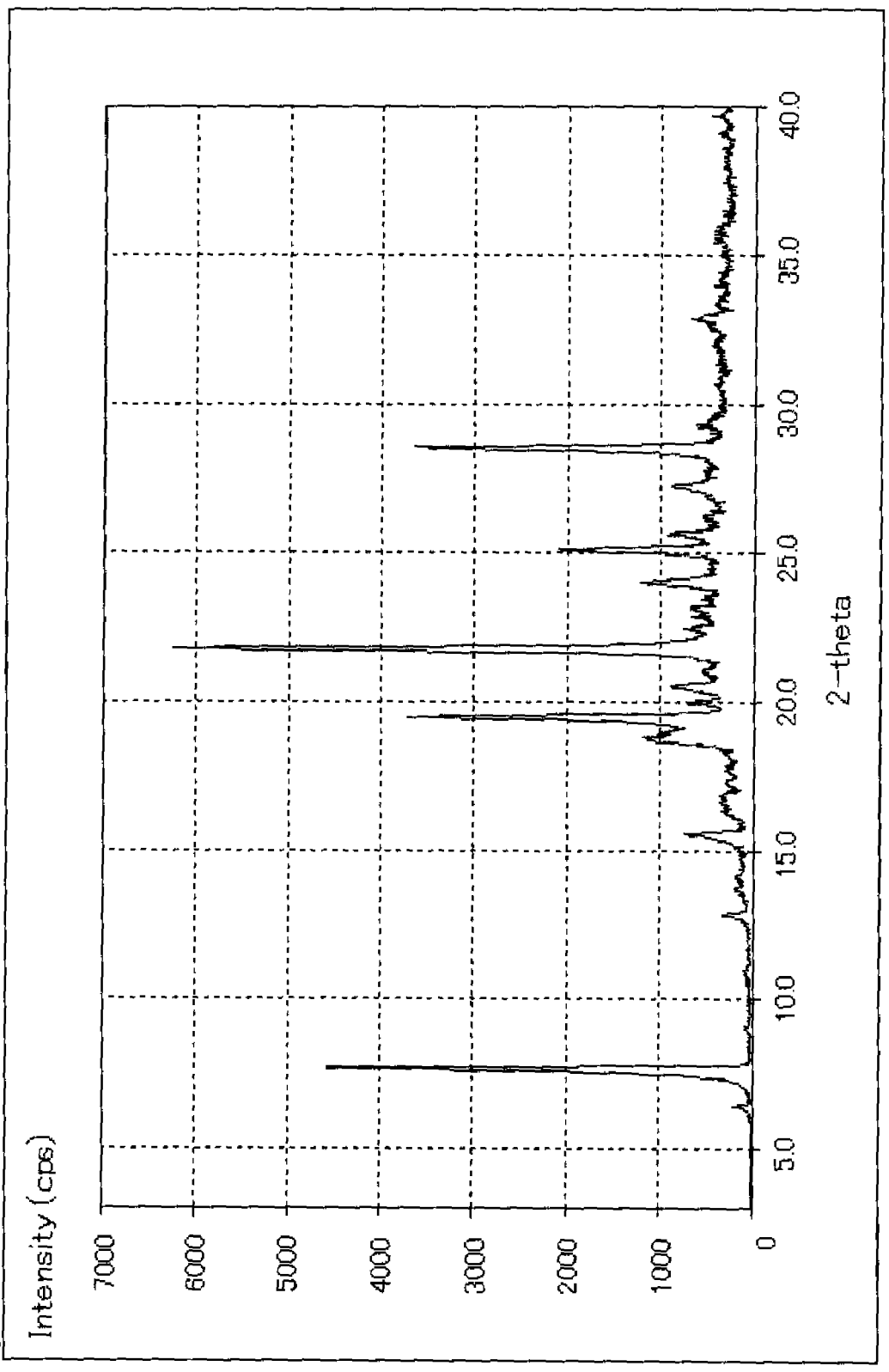
FIG. 13 is a graph showing the powder X-ray diffraction pattern of the crystal of a free base of the compound A. The crystal in the powder X-ray analysis using Cu as an anode, 2θ (°) shows the peaks, for example, at around 7.7, around 19.5, around 21.8, and around 28.6.
Figure 14:
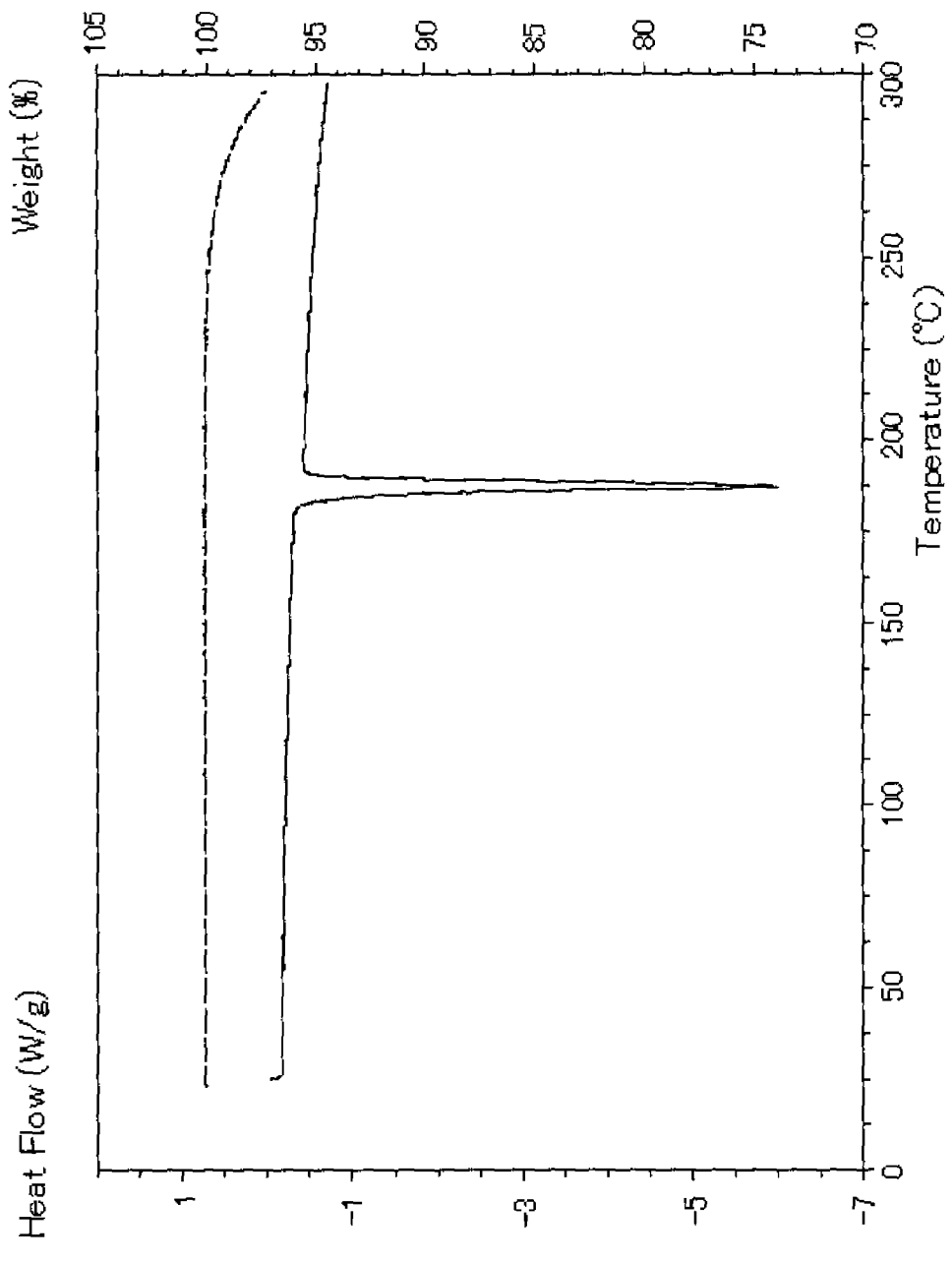
FIG. 14 is a graph showing the DSC curve of the crystal of a free base of the compound A. Endothermic onset temperature in DSC: ca. 185° C.

For FIGS. 3 and 13 Anode: Cu, wavelength: 1.54056 Å, measurement range: 2.50 to 40.00°, sampling interval: 0.02°, scan rate: 4.00°/min, tube voltage: 40 kV, tube current: 200 mA, divergence slit: variable (radiation width 5.00 mm), scattering slit: variable (radiation width 5.00 mm), receiving slit: 0.15 mm.

For FIGS. 1, 2, 4, 5, and 6, Anode: Cu, wavelength: 1.54056 Å, measurement range: 3.02 to 40.00°, sampling interval: 0.02°, scan rate: 3.00°/min, tube voltage: 40 kV, tube current: 200 mA, divergence slit: 1.00°, scattering slit: 1.00°, receiving slit: 0.15 mm.

Furthermore, the diffraction angle and diffraction intensity may vary more or less depending on the orientation of the crystal growth, the particle size, the measurement conditions, and so on. Accordingly, the values thereof should not be strictly solved.

In addition, the following abbreviations are used in Reference Examples, Examples, and Tables as below.

mp: melting point, FAB+: FAB-MS (M+H)$^+$, EI: EI-MS (M)$^+$, ESI+: ESI-MS (M+H)$^+$, NMR-DMSOd$_6$: δ (ppm) of the peaks in $^1$H-NMR in DMSO-d$_6$, DMF: N,N-Dimethylformamide, DMSO: Dimethylsulfoxide, THF: Tetrahydrofuran, 4 M hydrogen chloride/dioxane solution: 4 mol/l hydrogen chloride dioxane solution, MeCN: Acetonitrile, MeOH: Methanol, EtOH: Ethanol.

Reference Example 1

Preparation of the Compound a that is the Starting Compound of Examples 1 and 2

75.0 g of chloroisocyanuric acid and 680 mL of THF were added to a 2-L flask, followed by addition of 51.10 g of potassium carbonate at −19° C. under stirring. 41.08 g of p-fluoroaniline that has been diluted with 75 mL of THF at −12.4° C. or lower, and 75 mL of THF were added thereto. The reaction was carried out at −12.8 to −14.4° C. for 1 hour, and 450 mL of water was added. Liquid separation was carried out at room temperature to separate the aqueous layer, 300 mL of water was added thereto, and liquid separation was carried out again to separate the aqueous layer. To the organic layer were added an aqueous solution obtained by adding 1) 600 mL of THF, and 2) 1.1 g of potassium carbonate in 308 mL of water, and liquid separation was carried out to separate the aqueous layer. To the organic layer was added 150 mL of water, liquid separation was carried out to separate the aqueous layer, and the organic layer was concentrated under reduced pressure until the remaining amount of the solution became 280 mL. To the concentrated solution was added 750 mL of MeCN, and the concentration operation was carried out three times under reduced pressure until the remaining amount of the solution became 280 mL. Subsequently, 600 mL of MeCN was added thereto under cooling, followed by addition of 34.43 g of aniline and 75 mL of MeCN at −5.9° C. or less, and addition of 47.79 g of N,N-diisopropylethylamine and 38 mL of MeCN at −9.2° C. Thereafter, the temperature was elevated to room temperature, and after stirring for 12 hours, 48.42 g of 2-aminomethylpyrimidine and 75 mL of NeON were added thereto at room temperature, followed by addition of 57.35 g of N,N-diisopropylethylamine and 38 mL of NeON at room temperature. The inner temperature was elevated to 82.4° C., followed by stirring for 4.5 hours, and 560 mL of water was added thereto at an inner temperature of 70° C. or higher, followed by cooling. The crystal precipitation at an inner temperature of 65.8° C. was confirmed, followed by stirring at room temperature overnight, and filtration. The obtained crystals were washed with a mixed solution of MeCN:water=2:1, and subsequently washed with 300 mL of water. The obtained crystals were dried at 50° C. for 1 day under reduced pressure to obtain 108.54 g of a crystal of a free base of the compound A.

NMR-DMSOd$_6$:
4.71-4.73 (2H, m), 6.91-7.26 (5H, m), 7.37 (1H, dd, J=5.2 Hz, 4.8 Hz), 7.44-7.80 (5H, m), 8.78 (2H, d, J=4.8 Hz), 9.01-9.05 (2H, m).

FAB+: 389

Elemental Analysis. Calcd for $C_{20}H_{17}FN_8$: C, 61.85; H, 4.41; N, 28.85; F, 4.89; Cl, 0.00. Found: C, 61.78; H, 4.43; N, 28.81; F, 4.95; Cl, 0.00.

Example 1

Preparation of an "Anhydrous Salt Having a Ratio of the Compound A to Fumaric Acid of 2:1"

414 L of methyl ethyl ketone and 23.00 kg of the compound A were added to a reaction vessel 1, and dissolved at an inner temperature of 65.0° C. After filtration, the mixture was transferred to a reaction vessel 2, followed by heating again. 6.90 kg of fumaric acid and 115 L of EtOH were added to the reaction vessel 1, dissolved at an inner temperature of 58.3° C., transferred to the reaction vessel 2. After cooling, the crystallization was initiated at an inner temperature of 54.2° C., followed by stirring at 0° C. overnight. After filtration, the crystals were washed with 46 L of EtOH, and 30.34 kg of the obtained "crystal of the salt having a ratio of the compound A to fumaric acid of 1:1" (type III crystal: wet) and 460 L of EtOH were added to the reaction vessel 2. They were stirred at an inner temperature of 52.4 to 69.2° C. in a suspension state for 42 hours, cooled, and stirred at room temperature overnight. After filtration, the obtained crystals were washed with 46 L of EtOH, and then dried at 60° C. for 4 days under reduced pressure to obtain 20.97 kg of "crystals of an anhydrous salt having a ratio of the compound A to fumaric acid of 2:1" (type I).

A crystal of an anhydrous salt having a ratio of the compound A to fumaric acid of 2:1 (type I crystal)

NMR-DMSOd$_6$:
4.71-4.73 (2H, m), 6.64 (1H, s), 6.91-7.23 (5H, m), 7.37 (1H, dd, J=5.2 Hz, 4.8 Hz), 7.44-7.80 (5H, m), 8.78 (2H, d, J=4.8 Hz), 9.01-9.06 (2H, m), 13.06 (1H, br)

FAB+: 389

Elemental Analysis. Calcd for $C_{20}H_{17}FN_8.0.5C_4H_4O_4$: C, 59.19; H, 4.29; N, 25.10; F, 4.26; 0, 7.17. Found: C, 59.09; H, 4.36; N, 25.19; F, 4.31.

Endothermic onset temperature in DSC: ca. 190° C.

The powder X-ray diffraction pattern of the compound (type I crystal) of Example 1 is shown in FIG. 1.

A crystal of the salt having a ratio of the compound A to fumaric acid of 1:1 (the ratio of the compound A to methyl ethyl ketone as an residual solvent to EtOH to water=1:0.1:0.007:0.3) (type III crystal)

NMR-DMSOd$_6$
4.71 (2H, m), 6.64 (2H, s), 6.90-7.29 (5H, m), 7.38 (1H, dd, J=4.8 Hz, 4.8 Hz), 7.57-7.81 (5H, m), 8.79 (2H, d, J=4.8 Hz), 9.05-9.11 (2H, m), 13.09 (2H, br)

ESI+: 389

Elemental Analysis. Calcd for $C_{20}H_{17}FN_8.C_4H_4O_4.0.1C_4H_8.0.007 C_2H_6.0.3H_2O$: C, 56.67; H, 4.37; N, 21.66; F, 3.67; 0, 13.63. Found: C, 56.56; H, 4.47; N, 21.68; F, 3.63.

Endothermic onset temperature in DSC: ca. 160° C.

The powder X-ray diffraction pattern of the compound (type III crystal) of Example 1 is shown in FIG. 3.

Example 2

Preparation of a "Salt Having a Ratio of the Compound A to Fumaric Acid of 2:1, which is a Hydrate Having a Ratio of the Compound A to Water of 2:1" (Type II Crystal)

3.0 g of the crystal of the compound A, 120 mL of ethanol, and 30 mL of water were added to a 200 mL flask, heated to an inner temperature of 76° C. and dissolved. Subsequently, 448 mg of fumaric acid was added thereto, and dissolution was confirmed at an inner temperature of 80° C. It was cooled and stirred at room temperature overnight. It was filtered and dried at 40° C. to obtain 3.2 g of crystals of the "salt having a ratio of the compound A to fumaric acid of 2:1, which is a hydrate having a ratio of the compound A to water of 2:1" (type II crystal).

NMR-DMSOd$_6$
4.72-4.74 (2H, m), 6.65 (1H, s), 6.91-7.27 (5H, m), 7.37 (1H, dd, J=4.8 Hz, 4.8 Hz), 7.45-7.81 (5H, m), 8.78 (2H, d, J=4.8 Hz), 9.02-9.06 (2H, m), 13.06 (1H, br)

FAB+: 389

Elemental Analysis. Calcd for $C_{20}H_{17} FN_80.5C_4H_4O_4.0.5H_2O$: C, 58.02; H, 4.43; N, 24.60; F, 4.17; 0, 8.78. Found: C, 58.20; H, 4.46; N, 24.77; F, 4.33.

Endothermic onset temperature in DSC: ca. 150° C.

Figure 2:
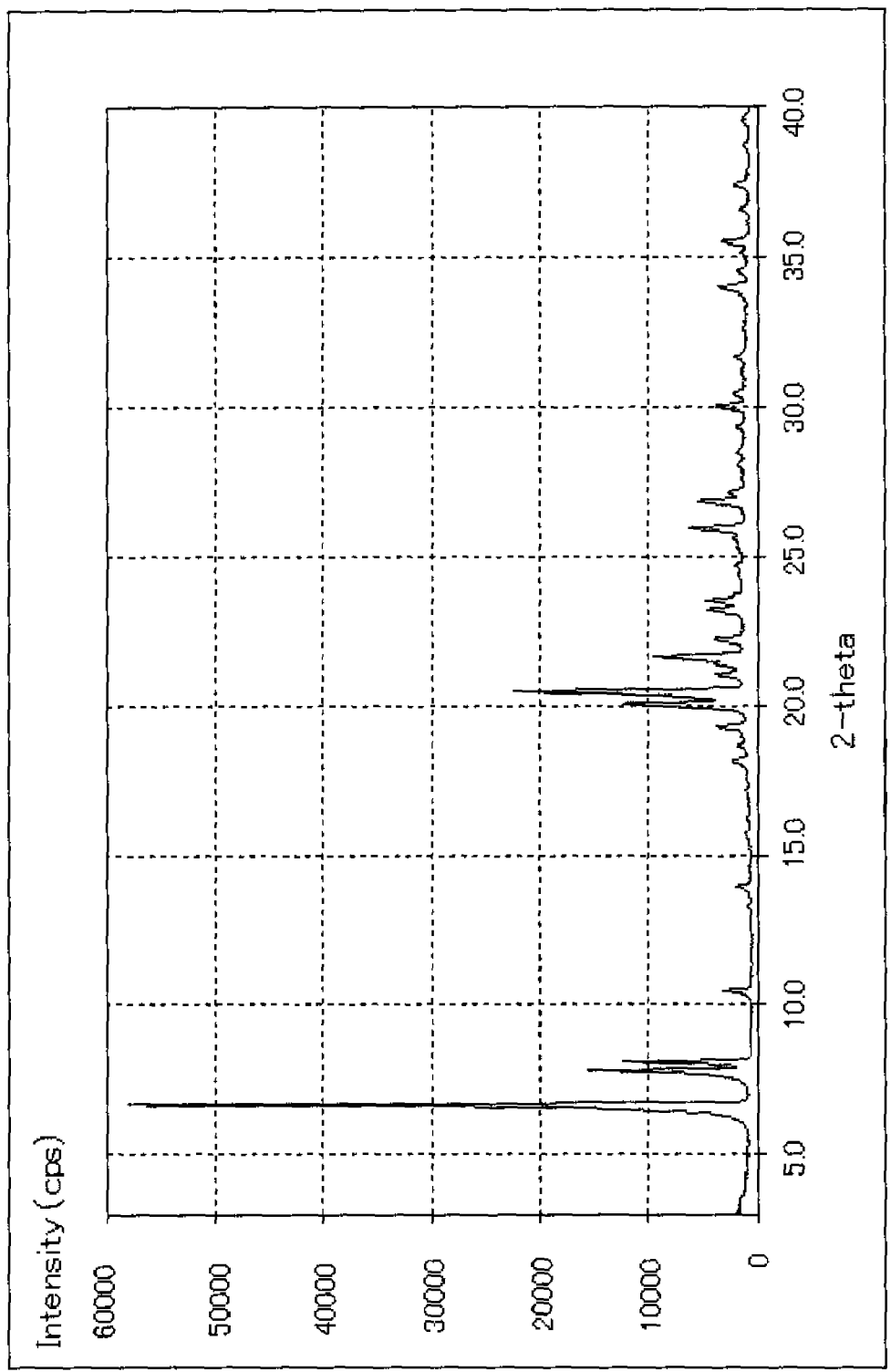
FIG. 2 is a graph showing the powder X-ray diffraction pattern of a crystal of a salt having a ratio of the compound A to fumaric acid of 2:1, which is a hydrate having a ratio of the compound A to water of 2:1 (type II crystal).

The powder X-ray diffraction pattern of the compound (type II crystal) of Example 2 is shown in FIG. 2.

Example 3

Preparation of a Salt Having a Ratio of the Compound B to Hydrogen Chloride of 1:2

To a suspension of 10.0 g of 6-chloro-N,N'-bis(4-fluorophenyl)-1,3,5-triazine-2,4-diamine in 100 mL of MeCN were added 6.0 g of 1-pyrimidin-2-yl methylamine acetate and 11.5 mL of N,N-diisopropylethylamine, followed by stirring at 85° C. for 12 hours. The reaction solution was cooled to room temperature, and to the residue obtained by removing the solvent by distillation was then added with ethyl acetate. The organic layer was washed with a 5% aqueous citric acid solution and brine, and dried over anhydrous magnesium sulfate, and the solvent was removed by distillation. The obtained residue was purified by silica gel column chromatography (chloroform: MeOH=100:0 to 95:5) to obtain 10.8 g as a light yellow amorphous. This was dissolved in 200 mL of EtOH, and 2 g of activated carbon was added thereto, followed by heating for 10 min under reflux. Then, the activated carbon was removed by filtration through a celite pad, and the residue obtained by removing the solvent by distillation was solidified using 400 mL of 80% aqueous EtOH to collect the solid by filtration, thereby obtaining 7.5 g as a colorless solid. This was heated and dissolved in 150 mL of 70% aqueous MeCN, followed by stirring at room temperature under leaving it to be cooled, and the precipitate was collected by filtration to obtain 7.08 g of the compound B.

7.05 g of the obtained compound B was dissolved in 200 mL of MeOH and 200 mL of THF, 10 mL of a 4 M hydrogen chloride/dioxane solution was added thereto, and the solvent was then removed by distillation. To the obtained residue was added EtOH, followed by stirring for 30 min to precipitate the solid. The solid was collected by filtration, dried under reduced pressure, then suspended in MeCN, and heated under reflux for 10 min, and the reaction solution was returned to at room temperature to give the solid, which was collected by filtration, and dried under reduced pressure to obtain 7.25 g of a "salt having a ratio of the compound B to hydrogen chloride of 1:2" as colorless crystals (type I crystal).

Figure 6:
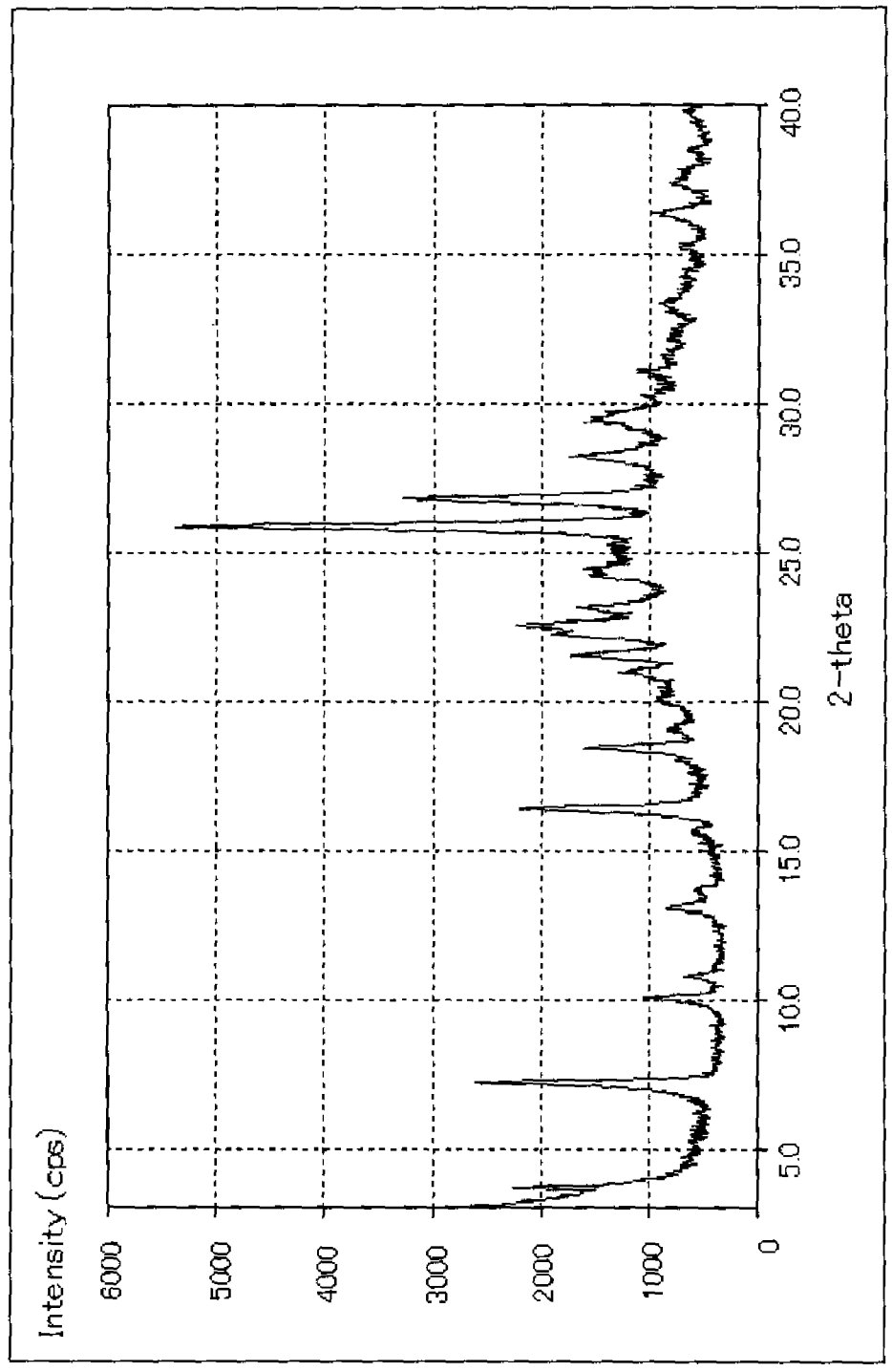
FIG. 6 is a graph showing the powder X-ray diffraction pattern of a crystal of a salt having a ratio of the compound B to hydrogen chloride of 1:2 (type I crystal).
Figure 7:
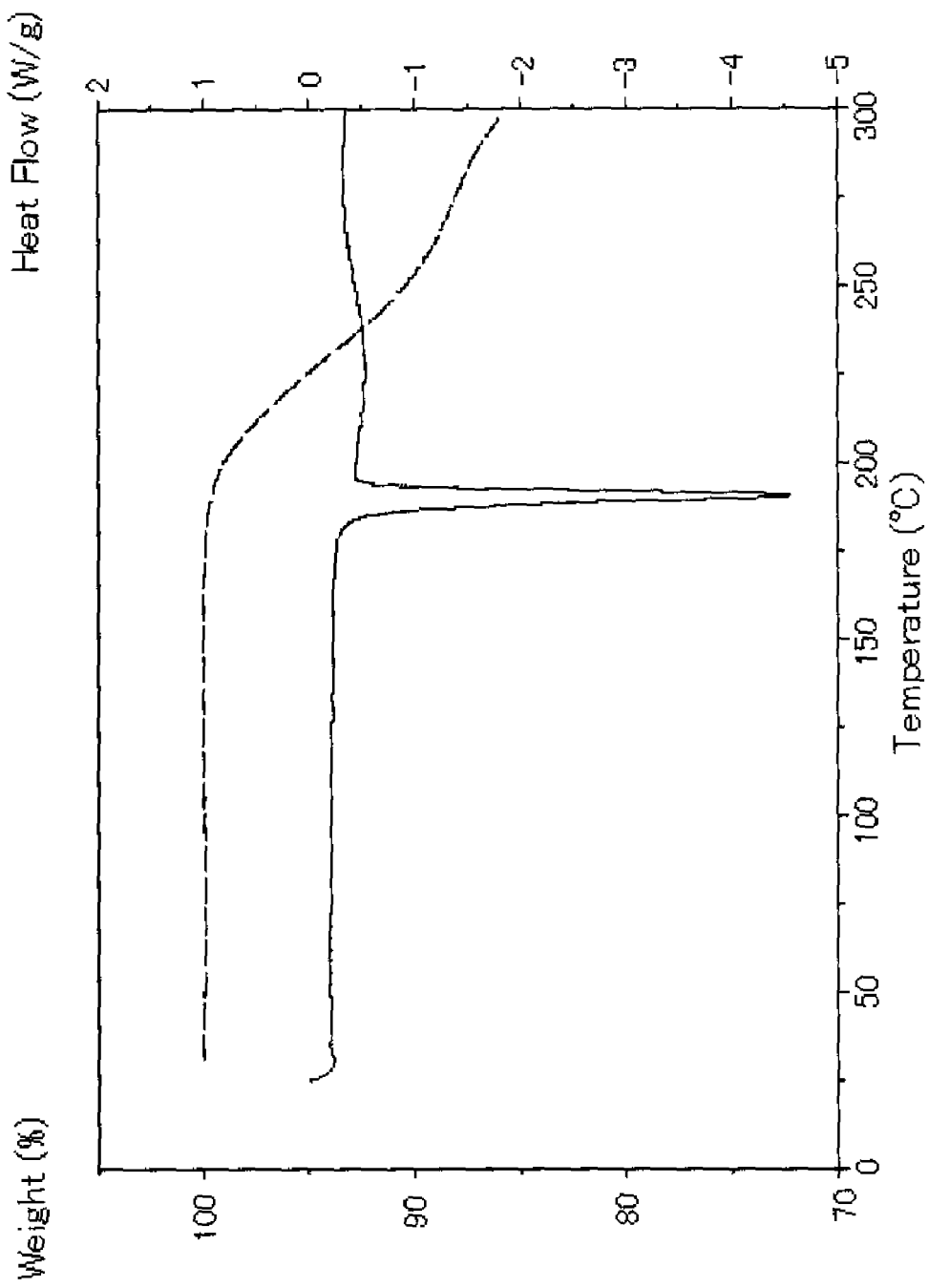
FIG. 7 is a graph showing the DSC curve of a crystal of an anhydrous salt having a ratio of the compound A to fumaric acid of 2:1 (type I crystal).
Figure 8:
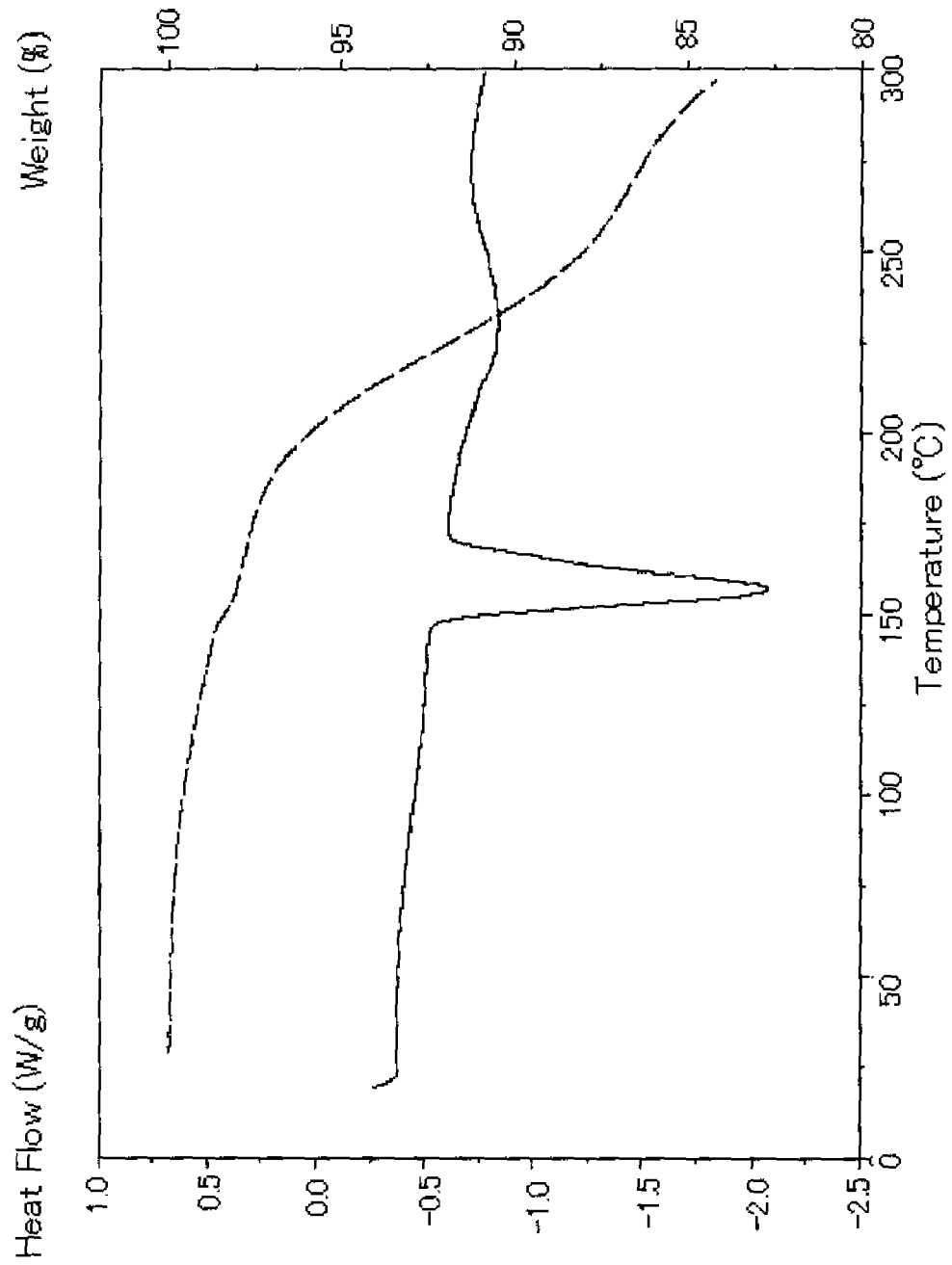
FIG. 8 is a graph showing the DSC curve of a crystal of a salt having a ratio of the compound A to fumaric acid of 2:1, which is a hydrate having a ratio of the compound A to water of 2:1 (type II crystal).
Figure 9:
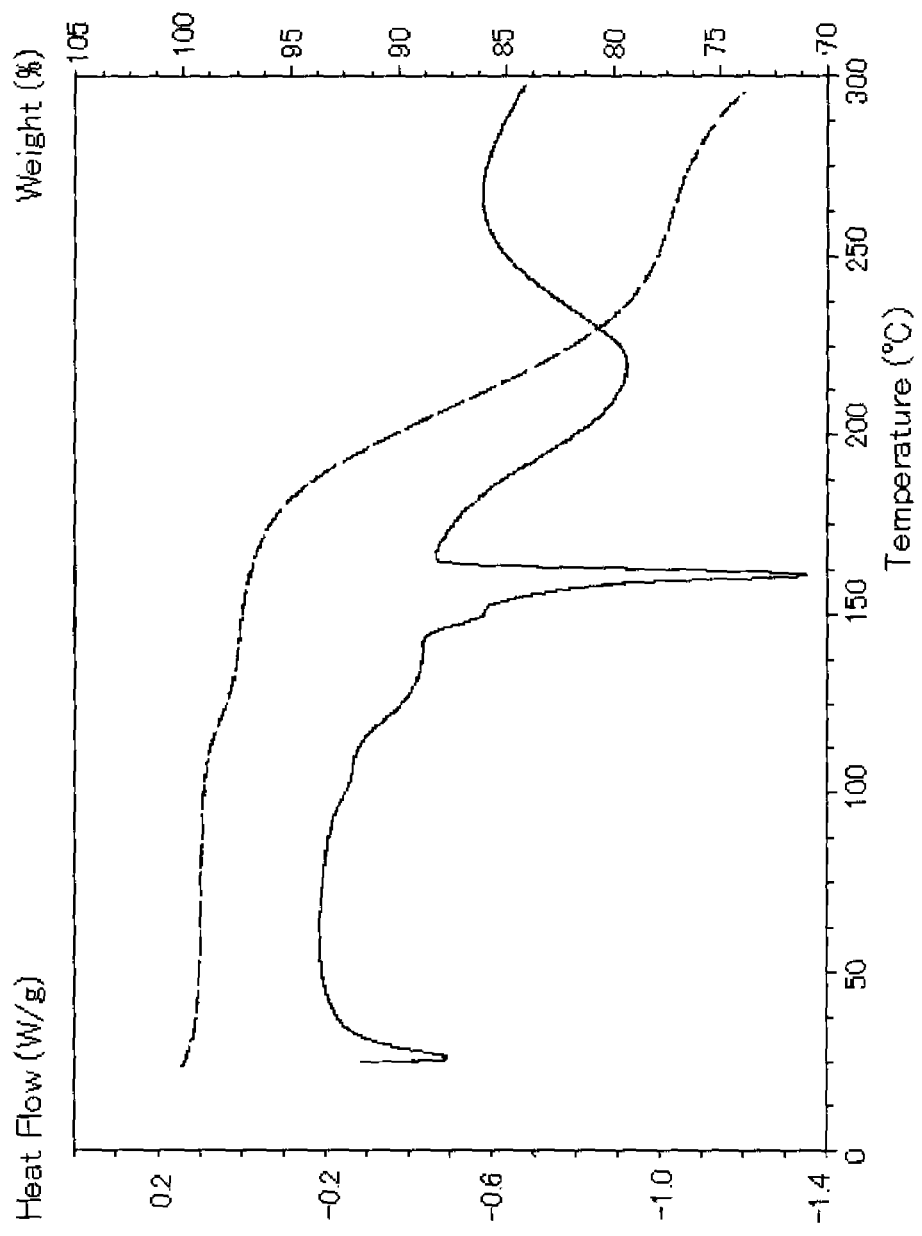
FIG. 9 is a graph showing the DSC curve of a crystal of a salt having a ratio of the compound A to fumaric acid of 1:1 (the ratio of the compound A to methyl ethyl ketone to EtOH to water that are residual solvents=1:0. 1:0.007:0.3) (type III crystal).
Figure 10:
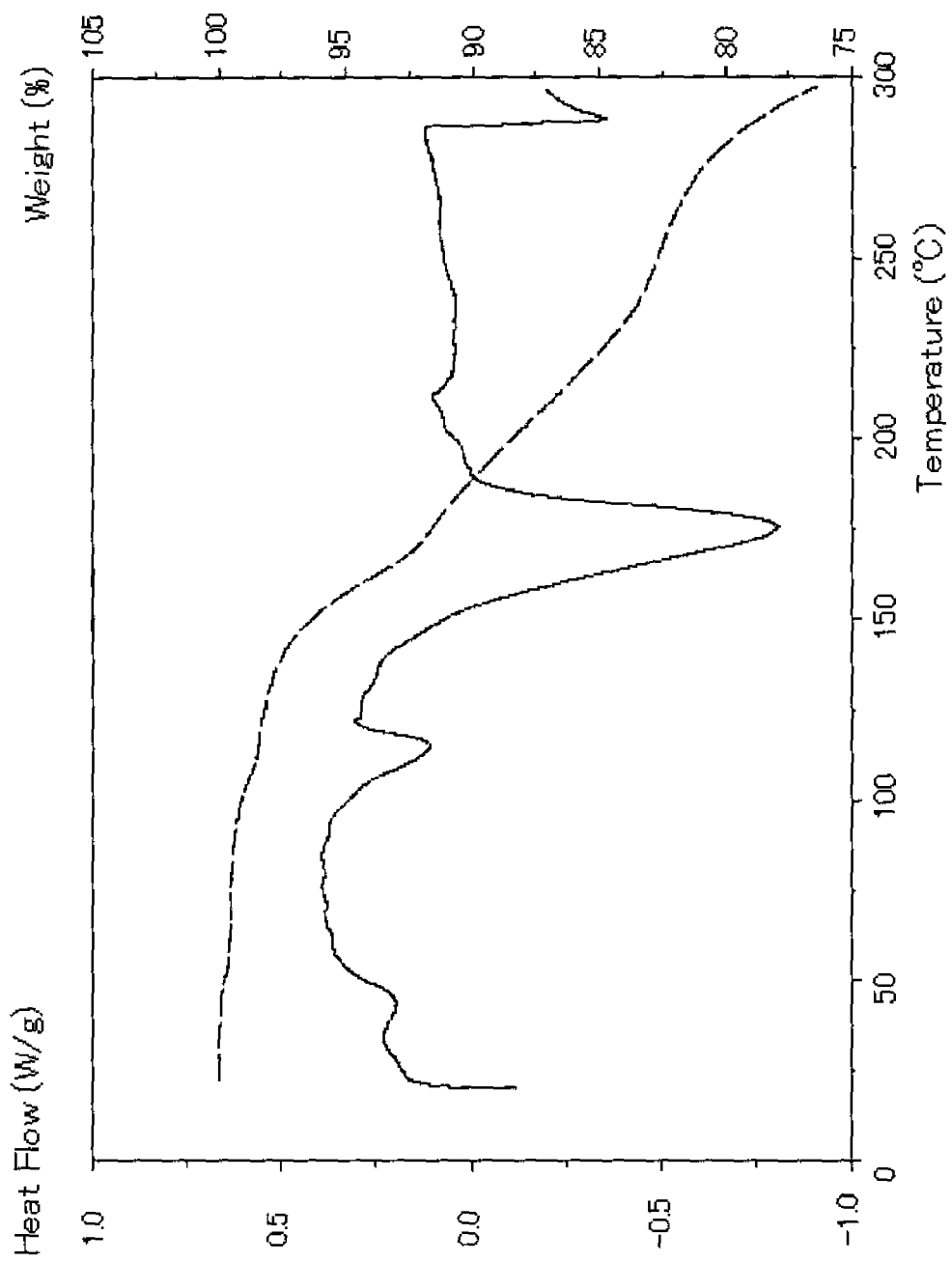
FIG. 10 is a graph showing the DSC curve of a crystal of an anhydrous salt having a ratio of the compound A to hydrogen chloride of 1:2.
Figure 11:
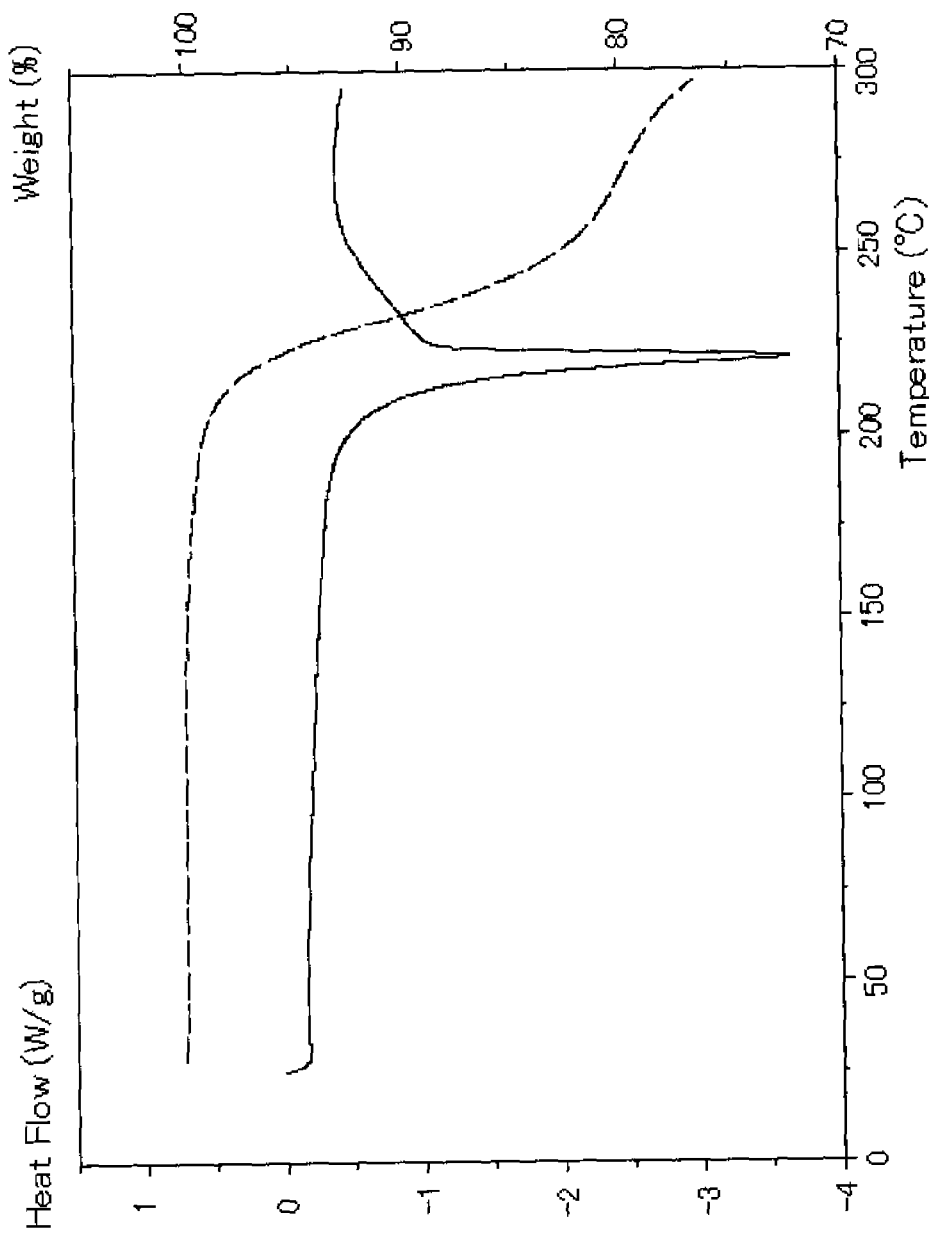
FIG. 11 is a graph showing the DSC curve of a crystal of a salt having a ratio of the compound B to fumaric acid of 1:1 (type I crystal).
Figure 12:
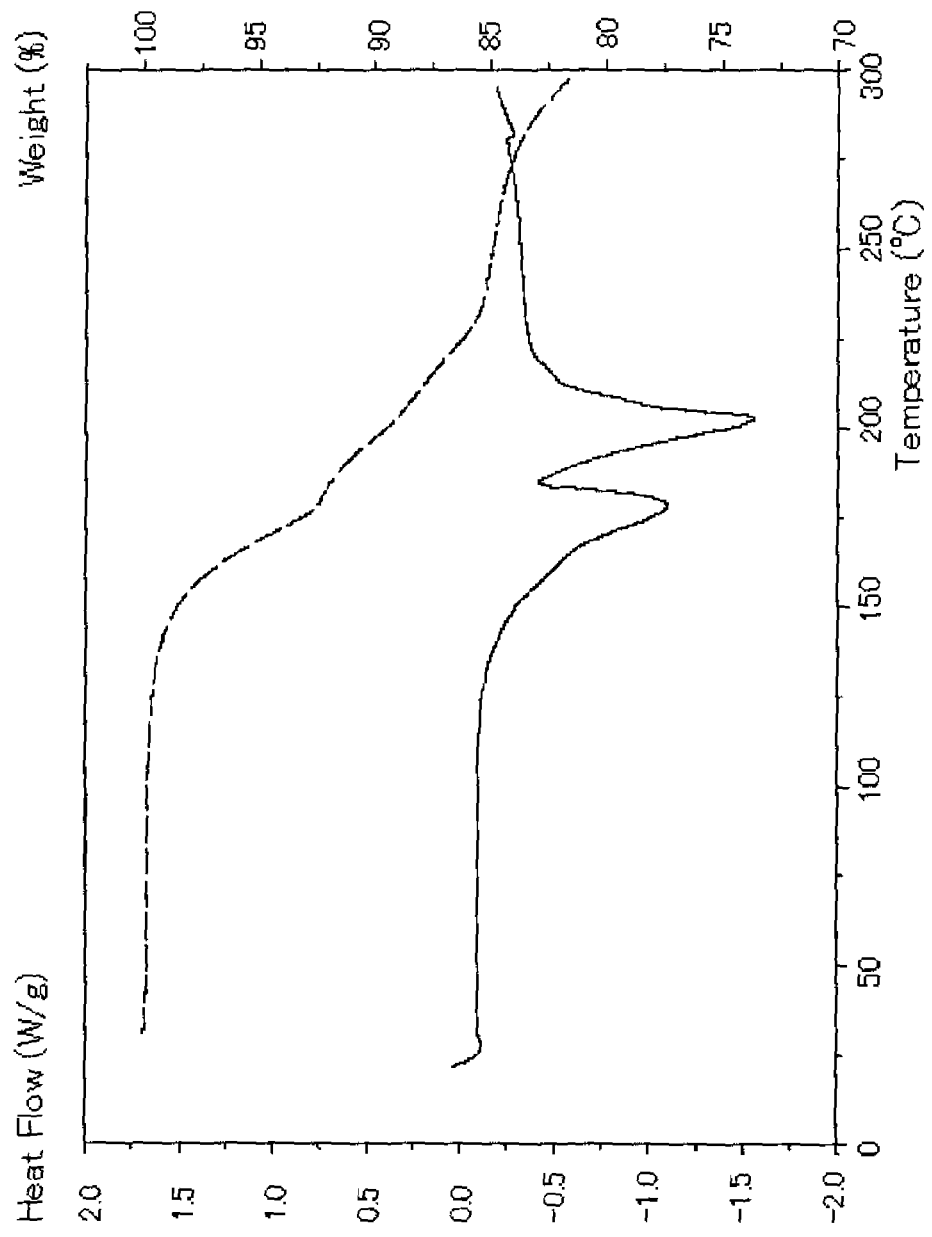
FIG. 12 is a graph showing the DSC curve of a crystal of a salt having a ratio of the compound B to hydrogen chloride of 1:2 (type I crystal).

Crystal of the salt having a ratio of the compound B to hydrogen chloride of 1:2
NMR-DMSOd$_6$
4.78 (2H, m), 7.10 (2H, brs), 7.25 (2H, t, J=8.7 Hz), 7.3-7.8 (6H, m), 8.85 (2H, d, J=4.9 Hz), 8.9-9.4 (1H, m), 10.45 (1H, brs), 10.88 (1H, brs)
Elemental Analysis. Calcd for $C_{20}H_{16}F_2N_8$.2HCl: C, 50.12; H, 3.79; N, 23.38; F, 7.93; Cl, 14.79. Found: C, 50.03; H, 3.92; N, 23.33; F, 7.94; Cl, 14.84.
Endothermic onset temperature in DSC: ca. 160, 190° C.
The powder X-ray diffraction pattern of the compound ((type I crystal)) of Example 3 is shown in FIG. 6.
Compound B (free base)
NMR-DMSOd$_6$
4.70 (2H, d, J=5.8 Hz), 7.00 (2H, m), 7.10 (2H, t, J=8.7 Hz), 7.38 (1H, t, J=4.9 Hz), 7.57 (3H, brs), 7.80 (2H, brs), 8.79 (2H, d, J=4.9 Hz), 9.0-9.2 (2H, m).
FAB+: 407

Example 4

Preparation of a Salt Having a Ratio of the Compound B to Fumaric Acid of 1:1

Figure 5:
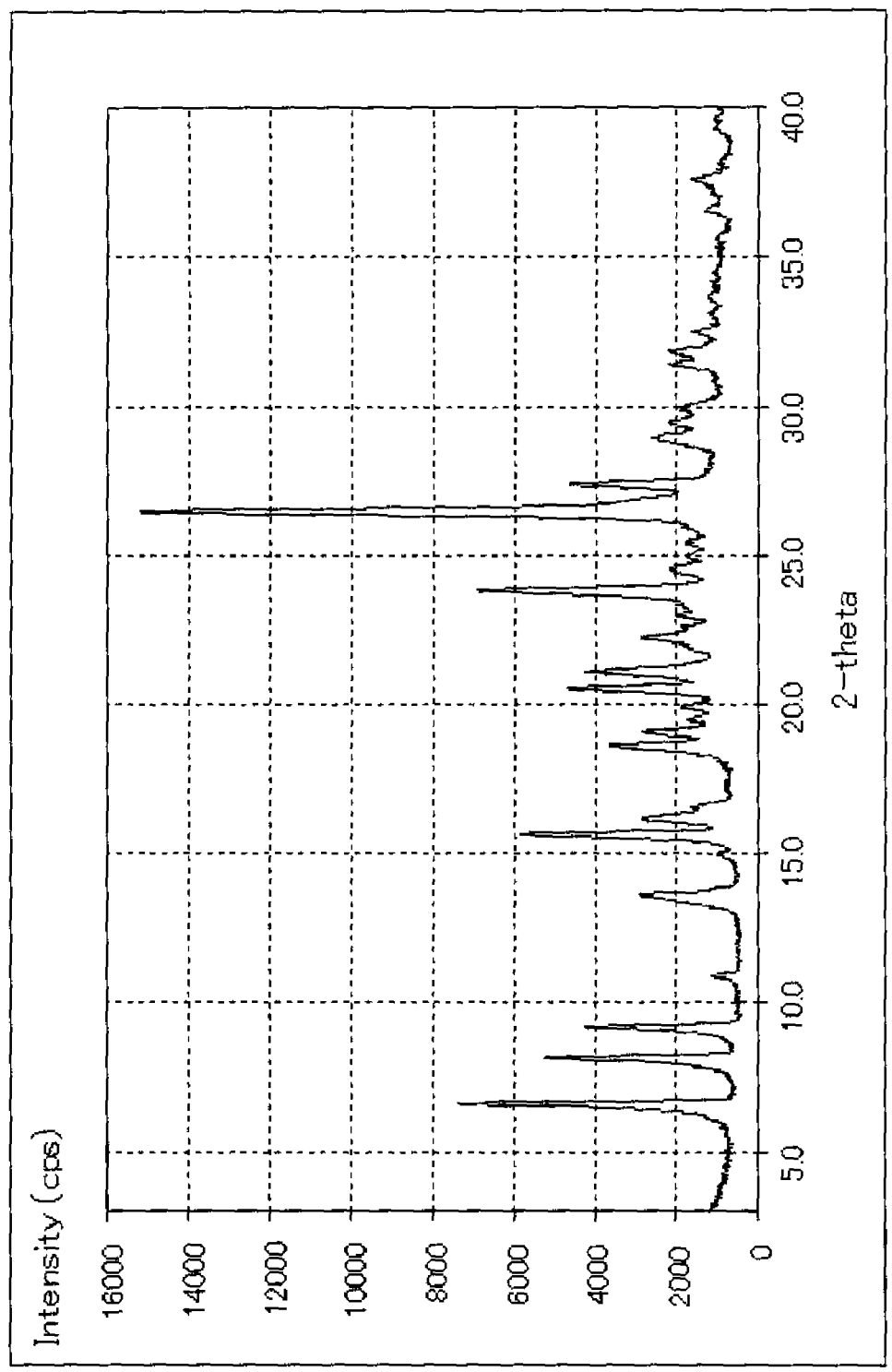
FIG. 5 is a graph showing the powder X-ray diffraction pattern of a crystal of a salt having a ratio of the compound B to fumaric acid of 1:1 (type I crystal).

To a solution of 1.0 g of the compound B in 50 mL of ethanol was added a solution of 285.6 mg of fumaric acid in 5 mL of ethanol. Soon, the precipitation of a solid was initiated. This reaction solution was heated under reflux to completely dissolve the solid, followed by stirring while leaving it to be cooled. When the inner temperature was lowered to 60° C., an extremely small amount of the crystal of the salt having a ratio of the compound B to fumaric acid of 1:1 was added thereto, followed by stirring at room temperature for 12 hours while leaving it to be cooled. The precipitated crystals were collected by filtration, washed with ethanol, and dried at 60° C. for 2 days under reduced pressure to obtain 970 mg of a "salt having a ratio of the compound B to fumaric acid of 1:1" as colorless crystals (type I crystal).
NMR-DMSOd$_6$
4.70 (2H, d, J=5.7 Hz), 6.64 (2H, s), 7.00 (2H, m), 7.10 (2H, t, J=8.7 Hz), 7.38 (1H, t, J=4.9 Hz), 7.57 (3H, brs), 7.80 (2H, brs), 8.80 (2H, d, J=4.9 Hz), 9.0-9.2 (2H, m), 13.13 (2H, brs).
Elemental Analysis. Calcd for $C_{20}H_{16}F_2N_8$.$C_4H_4O_4$: C, 55.17; H, 3.86; N, 21.45; F, 7.27. Found: C, 55.29; H, 4.05; N, 21.64; F, 7.32.
Endothermic onset temperature in DSC: ca 0.215° C.
The powder X-ray diffraction pattern of the compound (type I crystal) of Example 4 is shown in FIG. 5.
The effect of the acid addition salt of the compound A of the present invention was confirmed in the following Test Examples.

Test Example 1

Evaluation of Stability

Evaluation of the decomposed product during storage: Approximately 5 mg of a sample was metered into a 10 mL glass-made mass flask, a test was carried out in the following storage condition.
Condition 1: 70° C.-relative humidity 75%-opening-2 weeks
Condition 2: 70° C.-light shielding-sealing-2 weeks
Condition 3: 25° C.-D65 (3600 lux)-sealing-2 weeks
A dissolution solvent was filled to a marked line in a mess flask including the sample after storage, the dissolved solution was taken as a sample solution, and the compound A in the sample solution was quantitated. Furthermore, the detection of the compound A and compound B was carried out with UV at 266 nm and 254 nm, respectively and the handling of the devices including data processing was conducted in accordance to the methods and procedures as indicated in each device. (Device: LC-1100 Series manufactured by Agilent)
The results of these tests are shown in Table 1. Further, the quantitative value indicates the residual ratio of the compound A after the test to the compound A before the test.

TABLE 1

| Test condition | Quantitative Values (%) | | |
| --- | --- | --- | --- |
| | Example 1 | Example 2 | Example 4 |
| Condition 1 | 99 | 101 | 100 |
| Condition 2 | 99 | 100 | 100 |
| Condition 3 | 100 | 102 | 99 |

As shown in Table 1, it became apparent that the fumarate of the compound A and/or the fumarate of compound B has/have high stability against a high temperature and high humidity condition, a high temperature light-shielding condition, and light (Conditions 1 to 3).

Test Example 3

Therapeutic Effect of the Compound A and/or B for Schizophrenia

The therapeutic effect for Schizophrenia was proved by using a model for a methamphetamine-induced hyperlocomotion. Methamphetamine is a psychostimulant, and is known to cause symptoms that are similar to Schizophrenia by increasing the transmission in the dopaminergic neurons. The abnormal behavior produced when methamphetamine is administered to an animal is generally used as a screening method for a therapeutic drug for Schizophrenia (Oka et al., 1993, J. Pharmacol. Exp. Ther., 264:158-165, herein incorporated by reference). That is, a male ddY mouse was placed in an activity monitoring apparatus, and after 30 min, methamphetamine was administered. Immediately after administering methamphetamine, the mouse was returned to the monitoring apparatus, and the activity for 1 hour from immediately after the return was measured. For the measurement of the activity, a Supermex sensor manufactured by Muromachi Kikai Co., Ltd. was used. A solvent, or a diluted solution obtained by diluting each of the test compounds with a solvent at multiple concentrations was orally administered to mice in a group. As the solvent, a 0.5% aqueous methyl cellulose solution was used. The statistical analysis was carried out between the group administered with the solvent and the group administered with the drug, using a Dunnett's test.

Test Compound

Compound (1): Crystal of an anhydrous salt having a ratio of the compound A to fumaric acid of 2:1

Compound (2): Crystal of a salt having a ratio of the compound B to hydrogen chloride of 1:2

(Results)

The results of a methamphetamine-induced hyperlocomotion inhibitory action are shown in Table 2. The values in the table represent the respective minimum effective doses for the compound administered group (the smallest dose showing a significantly small activity with respect to the activity of the solvent administered group). The compounds A and B both inhibited the methamphetamine-induced hyperlocomotion. That is, it was found that these two compounds have an action of improving the symptoms of Schizophrenia.

TABLE 2

| Compound | Minimum effective dose (mg/kg p.o.) |
| --- | --- |
| (1) | 0.1 |
| (2) | 0.03 |

While the invention has been described in detail and with reference to specific embodiments thereof, it will be apparent to one skilled in the art that various changes and modifications can be made therein without departing from the scope thereof.

Industrial Applicability

A fumarate of N-(4-fluorophenyl)-N'-phenyl-N''-(pyrimidin-2-ylmethyl)-1,3,5-triazine-2,4,6-triamine (compound A) and/or a fumarate of N,N'-bis (4-fluorophenyl)-N''-(pyrimidin-2-ylmethyl)-1,3,5-triazine-2,4,6-triamine (compound B) are provided and useful as a medicament or a starting material for the having excellent stability and a novel crystal thereof.

The invention claimed is:
1. A crystal of an anhydrous salt having a ratio of a compound of the formula (I):

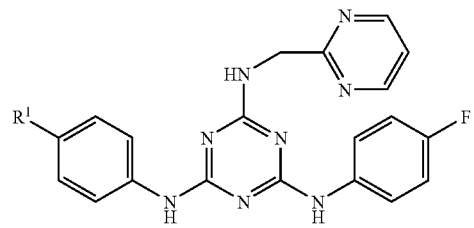

(I)

(wherein $R^1$ is H)
to fumaric acid of 2:1, which is a type I crystal.

2. A pharmaceutical composition including a crystal as described in claim 1 as an active ingredient, and further a pharmaceutically acceptable carrier.

3. A crystal of a salt having a ratio of a compound of the formula (I):

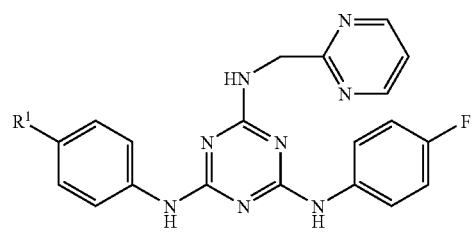

(I)

(wherein $R^1$ is H)
to fumaric acid of 2:1, which is a hydrate having a ratio of the compound of the formula (I) to water of 2:1, and which is a type II crystal.

4. A pharmaceutical composition including the crystal as described in claim 3 as an active ingredient, and further a pharmaceutically acceptable carrier.

5. A crystal of an anhydrous salt having a ratio of a compound of the formula (I):

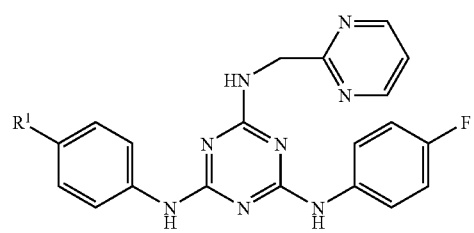

(I)

(wherein $R^1$ is H)
to fumaric acid of 1:1, which is a type III crystal.

* * * * *